(12) United States Patent
Smith et al.

(10) Patent No.: US 7,674,265 B2
(45) Date of Patent: Mar. 9, 2010

(54) MINIMALLY INVASIVE INSTRUMENTS AND METHODS FOR PREPARING VERTEBRAL ENDPLATES

(75) Inventors: Maurice M. Smith, Cordova, TN (US); Roy Lim, Memphis, TN (US); Thomas E. Roehm, III, Braden, TN (US)

(73) Assignee: Warsaw Orthopedic, Inc.

( * ) Notice: Subject to any disclaimer, the term of this patent is extended or adjusted under 35 U.S.C. 154(b) by 1702 days.

(21) Appl. No.: 10/422,221

(22) Filed: Apr. 24, 2003

(65) Prior Publication Data

US 2004/0215197 A1    Oct. 28, 2004

(51) Int. Cl.
*A61B 17/16* (2006.01)
(52) U.S. Cl. .................................................... 606/79
(58) Field of Classification Search ............. 606/79–86, 606/86 R, 90, 105; 600/201, 210, 214, 215, 600/217, 219, 222
See application file for complete search history.

(56) References Cited

U.S. PATENT DOCUMENTS

| 654,164 | A | * | 7/1900 | Lawrence ................... 175/288 |
|---|---|---|---|---|
| 3,702,611 | A | | 11/1972 | Fishbein |
| 3,750,652 | A | * | 8/1973 | Sherwin ...................... 606/90 |
| 5,015,255 | A | | 5/1991 | Kuslich |
| 5,062,845 | A | | 11/1991 | Kuslich et al. |
| 5,235,966 | A | * | 8/1993 | Jamner ....................... 600/204 |
| 5,445,639 | A | | 8/1995 | Kuslich et al. |
| 5,540,693 | A | * | 7/1996 | Fisher ......................... 606/79 |
| 5,591,170 | A | | 1/1997 | Spievack et al. |
| 5,601,556 | A | * | 2/1997 | Pisharodi ..................... 606/61 |
| 5,697,889 | A | * | 12/1997 | Slotman et al. ............. 600/204 |
| 5,776,054 | A | * | 7/1998 | Bobra ........................ 600/219 |
| 5,928,239 | A | | 7/1999 | Mirza |
| 6,083,228 | A | * | 7/2000 | Michelson ................... 606/79 |
| 6,159,214 | A | * | 12/2000 | Michelson ................... 606/80 |
| 6,224,604 | B1 | | 5/2001 | Suddaby |
| 6,383,188 | B2 | | 5/2002 | Kuslich et al. |
| 6,454,807 | B1 | * | 9/2002 | Jackson .................... 623/17.15 |
| 6,726,690 | B2 | * | 4/2004 | Eckman ....................... 606/79 |
| 6,840,944 | B2 | * | 1/2005 | Suddaby ..................... 606/105 |
| 2003/0009169 | A1 | * | 1/2003 | Young et al. ................. 606/86 |
| 2003/0135218 | A1 | | 7/2003 | Eckman |
| 2003/0225416 | A1 | * | 12/2003 | Bonvallet et al. ........... 606/105 |

FOREIGN PATENT DOCUMENTS

| WO | WO 01/60268 A1 | 8/2001 |
|---|---|---|
| WO | WO 02/102256 A1 | 12/2002 |
| WO | WO 2004/080316 A1 | 9/2004 |

* cited by examiner

*Primary Examiner*—Eduardo C Robert
*Assistant Examiner*—David Comstock

(57) ABSTRACT

Instruments and methods for treating vertebral endplates are disclosed. The instrument includes one or more treatment members movable from a reduced profile position for insertion to the operative site to a deployed position for providing treatment to the vertebral endplates.

42 Claims, 16 Drawing Sheets

MINIMALLY INVASIVE INSTRUMENTS AND METHODS FOR PREPARING VERTEBRAL ENDPLATES

BACKGROUND

Surgery for a patient can be painful and traumatic, particularly in the affected area of the patient's body. For example, the dissection and retraction required to access the surgical site in the patient can cause trauma to the dissected and retracted tissue as well as to the surrounding tissue. Tissue dissection and retraction can be required to insert instruments to a surgical site. To accommodate insertion, sufficient dissection and/or retraction of muscle tissue, nerve tissue, vasculature tissue and other tissue must be made to allow passage of the instrument therethrough.

Surgical instruments can include sharp elements which can cut or cause trauma to tissue in the approach to and adjacent the surgical site. Tissue dissection and retraction may be increased to avoid contact between the instrument and the tissue in the approach to the surgical site. Additionally, delicate anatomical structures may be present at or near the surgical site. Additional instruments or other precautions may be required to protect such tissue that limit or inhibit access to the surgical site.

For spinal surgical procedures, preparation of an endplate for ensuing fusion can require difficult maneuvering and gesturing of surgical instruments, such as curettes or scrapers, to cut or penetrate the bony material of the endplate. Sufficient time and effort during the surgery must be devoted to the use such instruments to obtain the desired result.

There remains a need for instruments and methods that can be employed for preparing a surgical site that minimize tissue dissection and retraction and exposure of the anatomical structures at the surgical site to sharp elements of the instruments. There further remains a need for instruments and methods that can be efficiently and effectively employed for preparing vertebral endplates for ensuing fusion. The present invention is directed to meeting these needs, among others.

SUMMARY

A treatment instrument is provided that includes a treatment member movable between deployed and undeployed positions. In the undeployed position, the at least one treatment member is positionable to a surgical site without exposing the anatomical structures to sharp edges of the treatment member. In the deployed position, the treatment member includes at least one treatment portion adapted to treat a vertebral endplate positioned adjacent the treatment member. The treatment of the vertebral endplate includes penetrating, crushing and/or removing bone material to induce bleeding to promote subsequent fusion of adjacent vertebrae in a spinal fusion procedure.

DESCRIPTION OF THE ILLUSTRATED EMBODIMENTS

Figure 1:
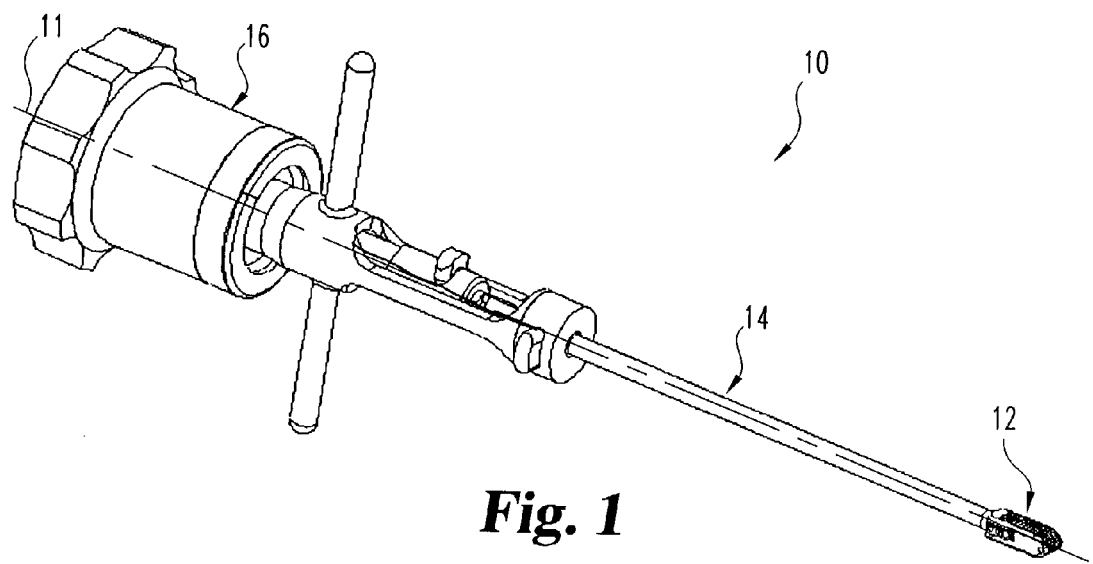
FIG. 1 is a perspective view of one embodiment of an endplate treatment instrument.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated therein are contemplated as would normally occur to one skilled in the art to which the invention relates.

Figure 2:
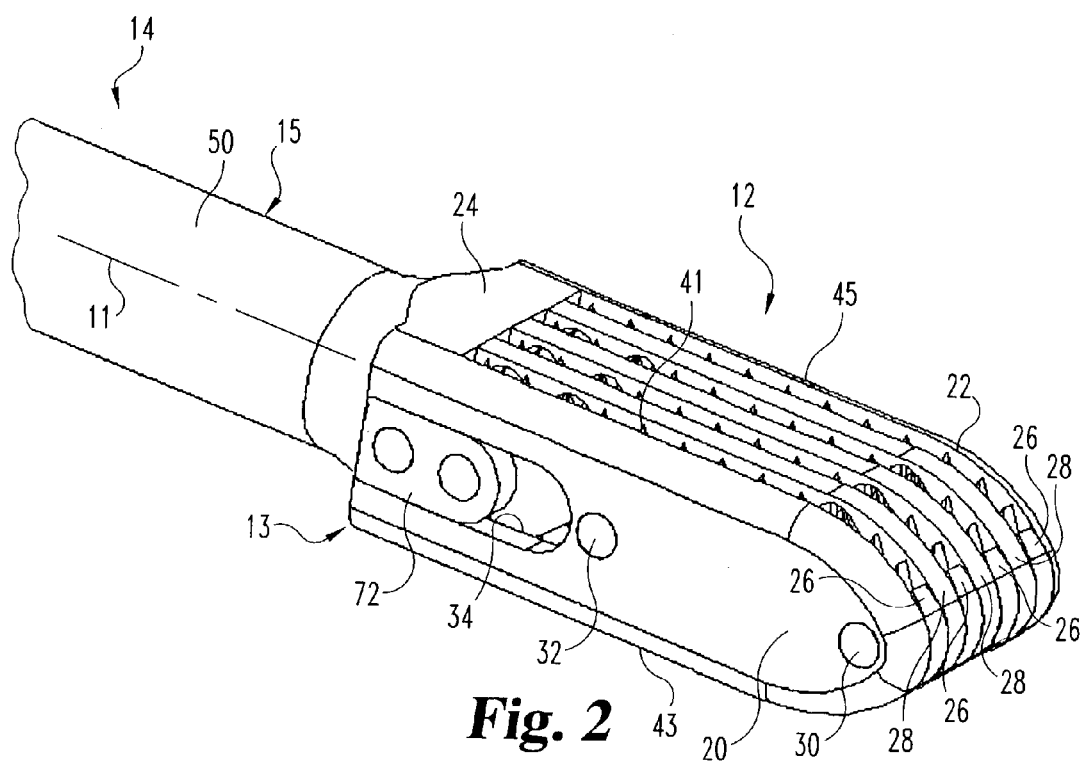
FIG. 2 is a perspective view of the distal portion of the instrument of FIG. 1 in an undeployed position.
Figure 3:
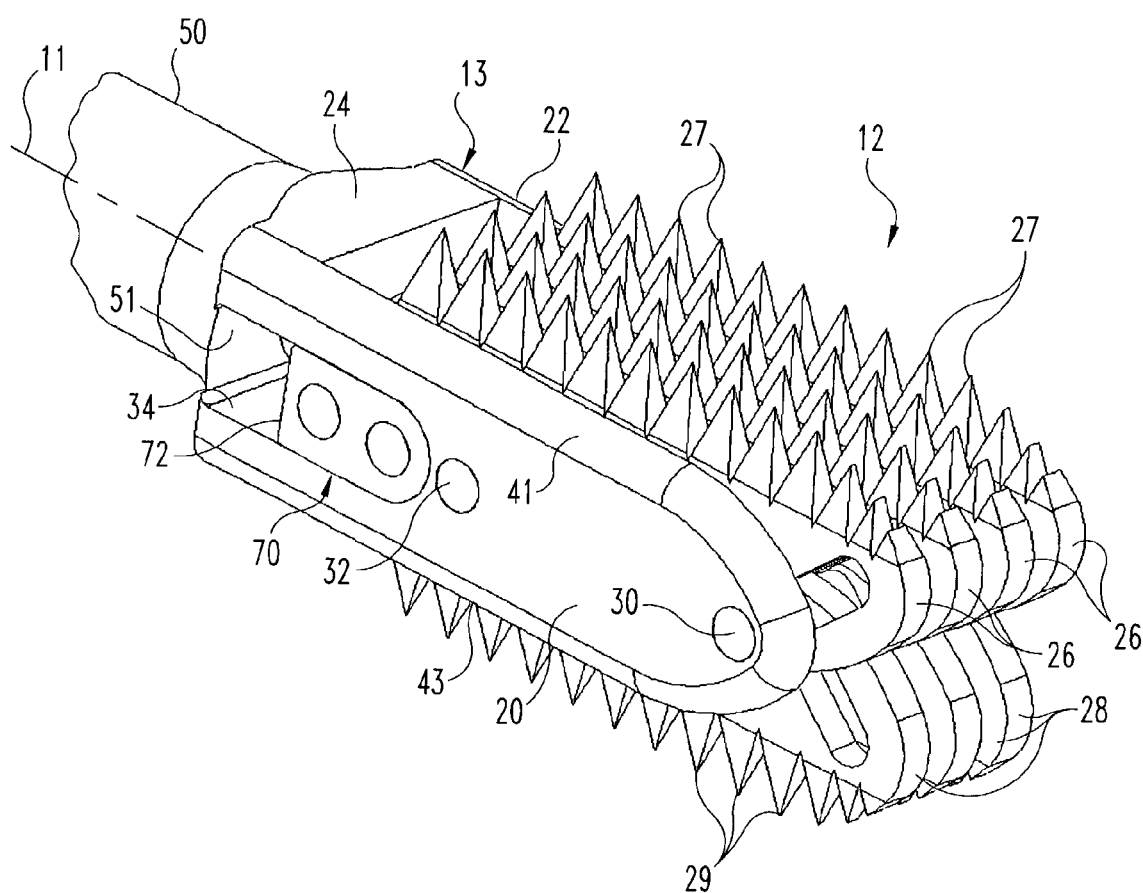
FIGS. 3 and 4 are perspective views of the distal portion of the instrument of FIG. 1 in a deployed position.
Figure 4:
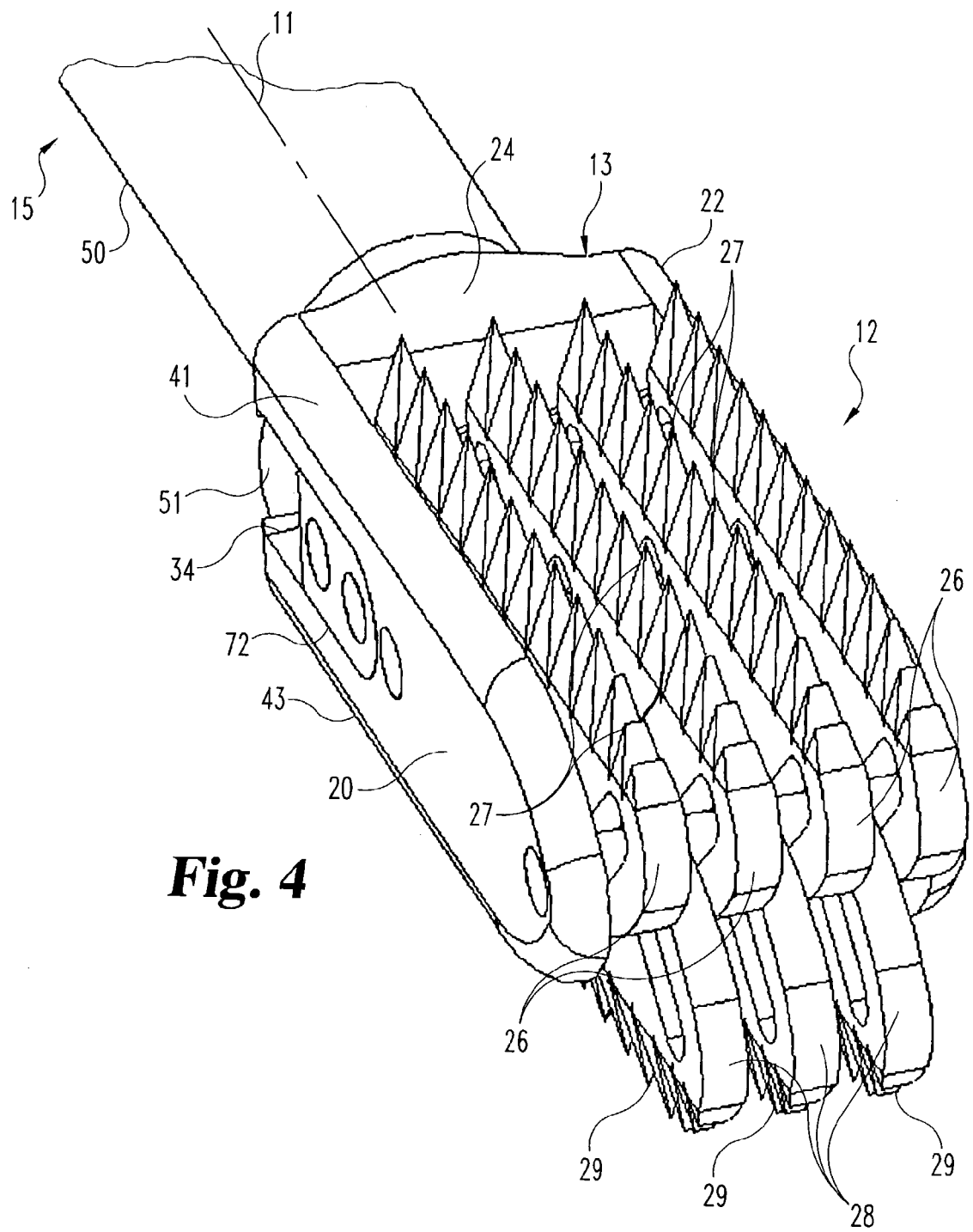

Referring to FIG. 1, there is shown an endplate treatment instrument 10. Treatment instrument 10 includes a distal treatment system 12, a proximal handle assembly 16, and an actuating assembly 14 extending therebetween. Treatment system 12 is positionable in a spinal disc space between adjacent endplates of a pair of opposing vertebrae. Treatment treatment system 12 includes an undeployed position, as shown in FIGS. 1 and 2, for insertion through a passageway through skin and tissue to the desired operative location. Treatment instrument 10 can be manipulated to move treatment system 12 to a deployed position, as shown in FIGS. 3 and 4, where the treatment members project outwardly to treat the adjacent vertebral endplates. When the desired endplate treatment has been obtained, treatment instrument 10 can be manipulated to return treatment system 12 to its undeployed position for repositioning in the disc space for further treatments or for withdrawal from the patient through the passageway.

Treatment system 12 includes a plurality of first treatment members 26 and a plurality of second treatment member 28. Treatment members 26 each include a plurality of treatment portions 27 extending from one side thereof. Treatment member 28 includes a plurality of treatment portions 29 extending from one side thereof in a direction opposite treatment portions 27. In the illustrated embodiment, treatment members 26 include treatment portions 27 oriented in the same direction and are separated from one another by a treatment member 28 that includes treatment portions 29 oriented in the direction opposite the orientation of treatment portions 27. Other embodiments contemplate that two or more of the treatment members 26 and/or treatment members 28 are positioned directly adjacent one another. Still other embodiments contemplate a treatment instrument 10 with treatment portions that extend in only one direction when the treatment members are deployed.

In the illustrated embodiment, treatment portions 27, 29 provide a serrated surface along the respective treatment member 26, 28. The treatment portions 27, 29 include a plurality of pyramidally shaped spikes having a sharpened outer end to penetrate bone material of the vertebral endplate when deployed. Other shapes and forms are also contemplated for treatment portions 27, 29. For example, treatment portions 27, 29 could include a plurality or series of elongated blades or sharp edges that extend transversely to a longitudinal axis 11 of treatment instrument 10. In another example, treatment portions 27, 29 include one or more sharp edges that extend along the longitudinal axis 11 of treatment instrument 10. Still other embodiments contemplate treatment portions 27, 29 in the form of spikes, barbs, or teeth with sharp ends. It is also contemplated that treatment portions 27, 29 can include blunt ends that crush the adjacent bony structure when deployed.

In the undeployed position of FIG. 2, treatment members 26, 28 are substantially enclosed within a mounting portion 13 at the distal end of treatment instrument 10. As such, mounting portion 13 prevents treatment portions 27, 29 from contacting tissue or other anatomical structures as treatment system 12 is advanced to the desired location at the operative site. In the deployed position of FIGS. 3 and 4, treatment portions 27, 29 are moved transversely to longitudinal axis 11 and extend outwardly from mounting portion 13 to engage the adjacent bony structure to provide treatment thereto.

Treatment portions 27, 29 can at least partially penetrate, crush, or otherwise form openings in the bony material of the vertebral endplates when deployed. This promotes bleeding of the vertebral endplates and facilitates bone growth and implant incorporation in interbody fusion procedures. Treatment portions 27, 29 can be withdrawn and redeployed as needed to provide the desired penetration and/or bleeding of the endplates. It is further contemplated that treatment instrument 10 can be manipulated with treatment portions 27, 29 deployed to provide further endplate treatment. For example, treatment instrument 10 can be moved in the proximal-distal directions, laterally, and/or rotated in the disc space in small strokes with treatment portions 27, 29 deployed. When the desired treatment has been obtained, treatment portions 27, 29 can be withdrawn into mounting portion 13, allowing withdrawal of treatment system 12 from the disc space and the patient's body without exposing tissue, nerves and other anatomical structures to treatment portions 27, 29.

Figure 5:
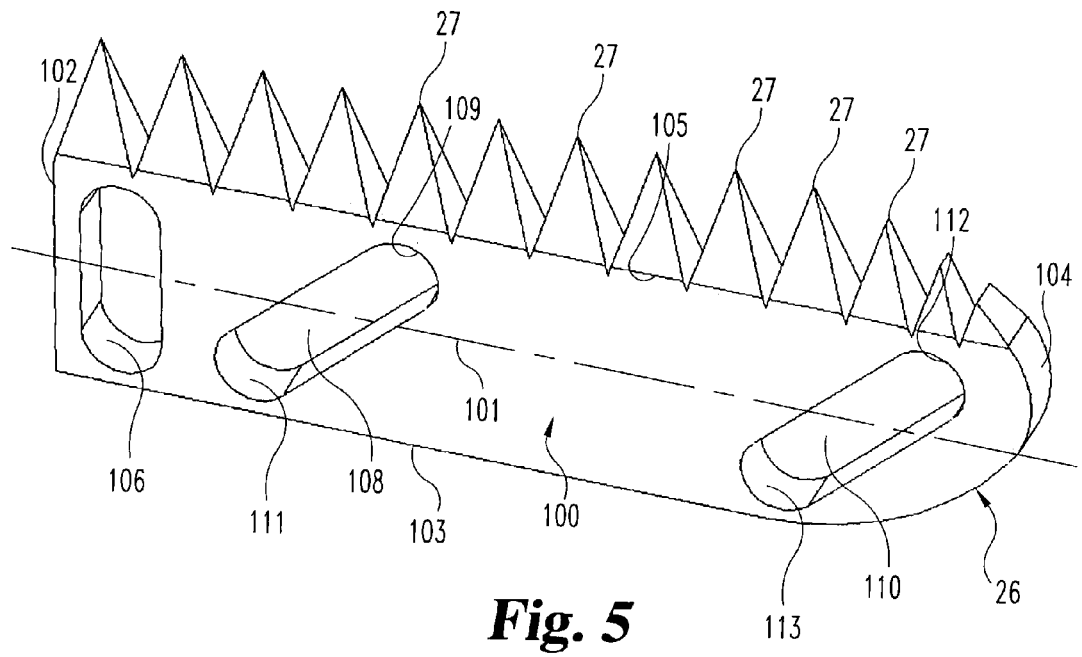
FIG. 5 is a perspective view showing a treatment member comprising a portion of the instrument of FIG. 1.

Referring to FIG. 5, further details regarding treatment member 26 will be provided, it being understood that treatment member 28 can be substantially identical thereto. Treatment member 26 includes an elongated body portion 100 extending between a proximal end 102 and a distal end 104 along longitudinal axis 101. Treatment portions 27 are spaced along longitudinal axis 101 and extend from a first side 105 of body portion 100. Body portion 100 includes a second side 103 extending along longitudinal axis 101 opposite treatment portions 27. Second side 103 includes a smooth surface profile along longitudinal axis 101. To facilitate insertion of treatment member 26 in its undeployed position in mounting portion 13, second side 103 can includes a curved profile adjacent distal end 104 so that distal end 104 has a blunt nose and reduced height relative to proximal end 102. First side 105 extends substantially parallel to longitudinal axis 101, offsetting the blunt nose at distal end 104 from longitudinal axis 101 toward first side 105.

Figure 8:
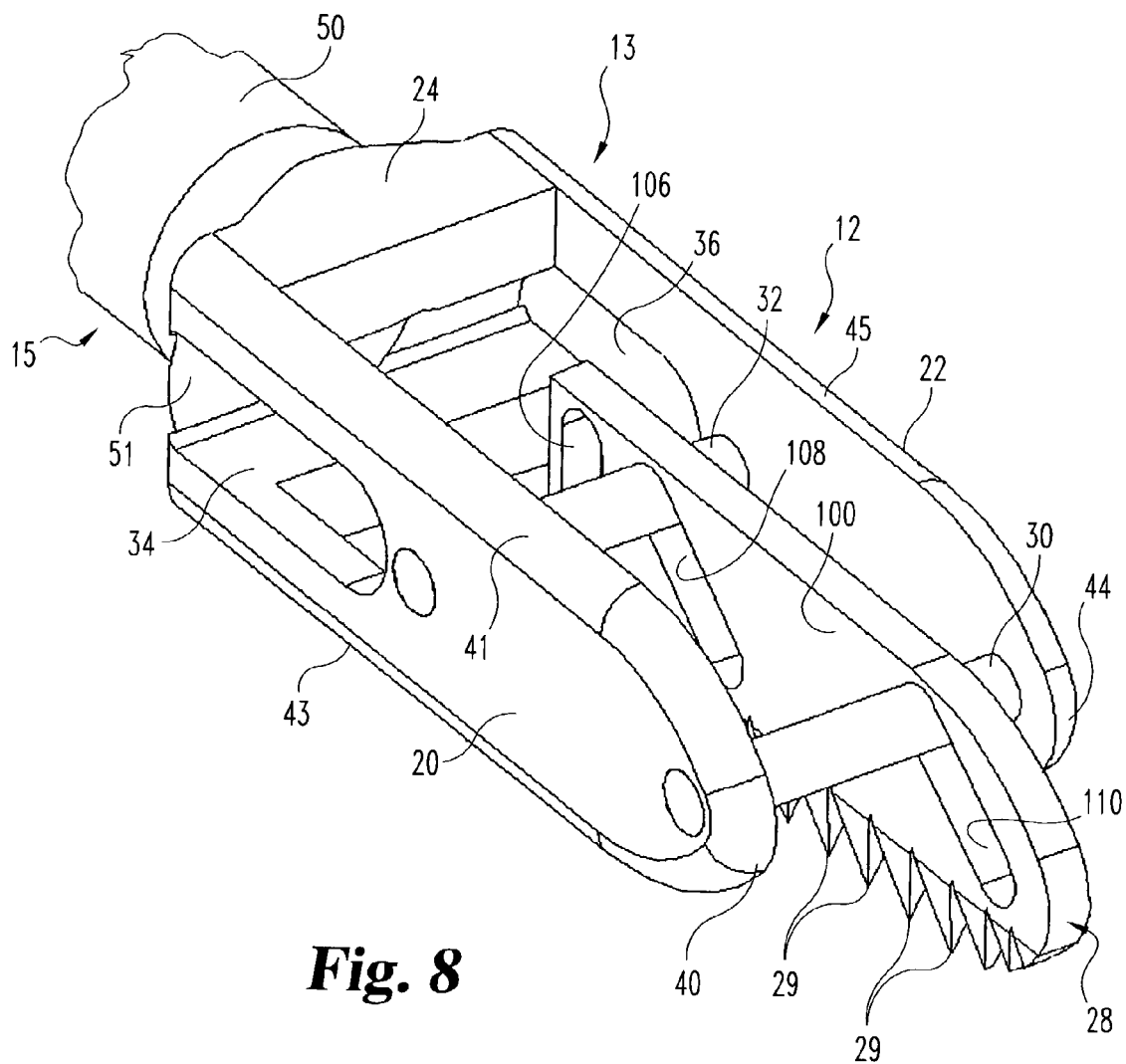
FIG. 8 is a perspective view showing the distal portion of the mounting member of FIG. 7 with the treatment member of FIG. 5 mounted thereto and oriented in a direction opposite that of the treatment member of FIG. 7.

Body portion 100 includes a proximal slot 106 orthogonally oriented to longitudinal axis 101. Body portion 100 further includes a proximal passage 108 and a distal passage 110. Passages 108, 110 are inclined relative to longitudinal axis 101 so that passage 108 includes a distal end 109 and a proximal end 111, and passage 110 includes a distal end 112 and a proximal end 113. Distal ends 109, 112 are offset from longitudinal axis 101 and positioned adjacent treatment portions 27, and proximal ends 111, 113 are offset from longitudinal axis 101 and positioned adjacent second side 103. Treatment member 28 similarly includes a body portion 100 including a proximal slot 106, a proximal passage 108, and a distal passage 110, as shown in FIG. 8.

Figure 9:
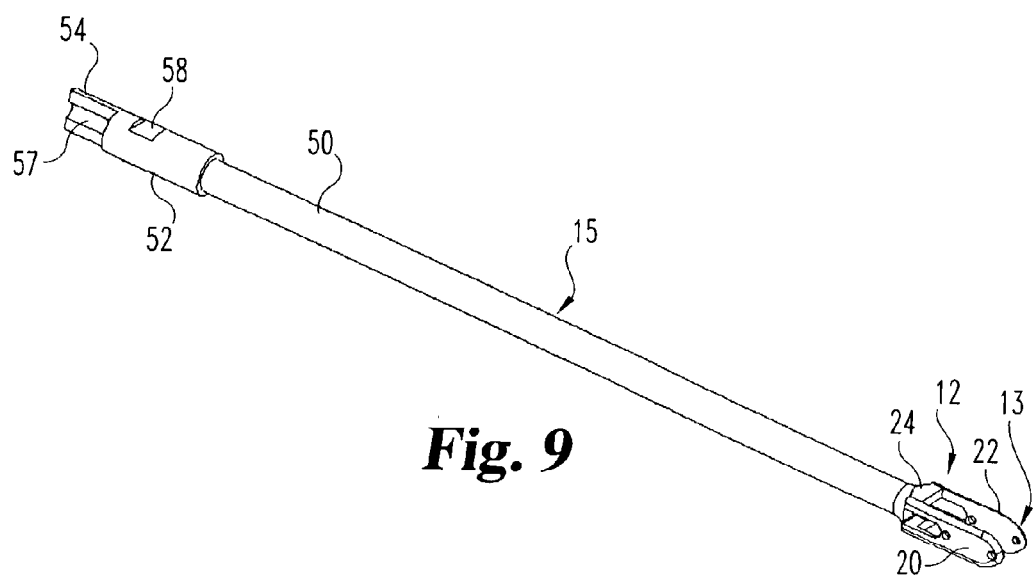
FIG. 9 is a perspective view of the mounting member comprising a portion of the treatment instrument of FIG. 1.
Figure 10:
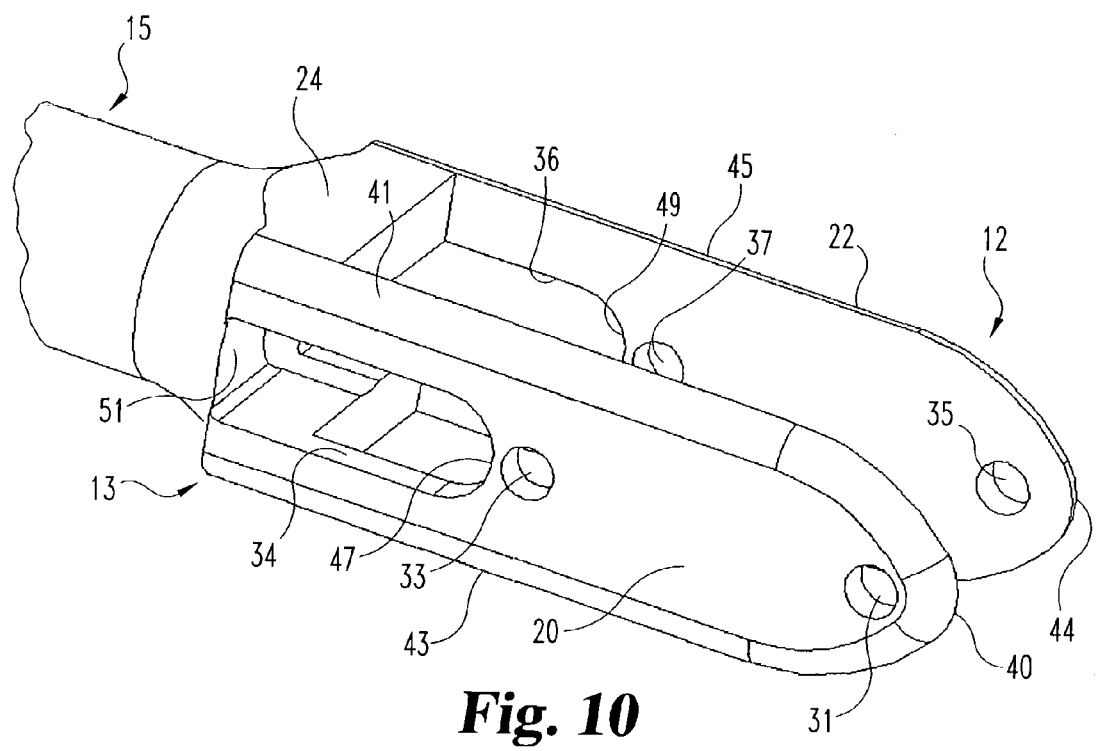
FIG. 10 is a perspective view of the distal end portion of the mounting member of FIG. 9.

Referring further to FIGS. 7-10, mounting of treatment system 12 to mounting portion 13 of instrument 10 will be further discussed. Mounting portion 13 is provided at the distal end of a mounting member 15 of actuator assembly 14, as shown in FIGS. 9 and 10. Mounting member 15 includes a shaft 50 extending between a proximal end boss 52 and mounting portion 13. Mounting portion 13 includes a first flange member 20 spaced from a second flange member 22. Flange members 20, 22 extend distally from an end member 24 at the distal end of shaft 50. Flange members 20, 22 extend along and are offset laterally from longitudinal axis 11, providing upper and lower openings and a distal end opening therebetween.

Flange member 20 includes a side opening 34 extending from a distal end wall 51 of end member 24 distally along a portion of the length of flange member 20. Similarly, flange member 22 includes a side opening 36 extending from distal end wall 51 of end member 24 along a portion of the length of flange member 22. A distal guide pin 30 extends between and is secured in holes 31, 35 adjacent the distal end noses 40, 44 of flange members 20, 22. A proximal guide pin 32 extends between and is secured in holes 33, 37 located about midlength along flange members 20, 22 and distally of side openings 34, 36. Flange member 20 includes distal end nose 40 having a blunt rounded shape, and flange member 22 includes distal end nose 44 having a blunt rounded shape. The blunt rounded shape facilitates insertion through tissue and into the space between adjacent vertebrae.

Figure 6:
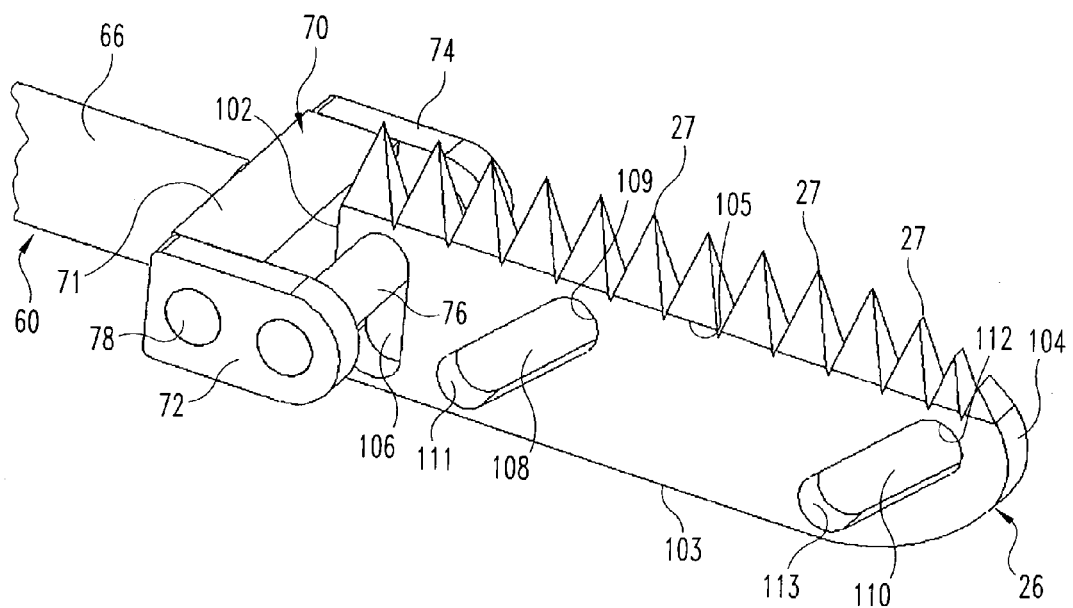
FIG. 6 is a perspective view showing the treatment member of FIG. 5 coupled to a distal portion of an actuating member of the treatment instrument of FIG. 1.
Figure 7:
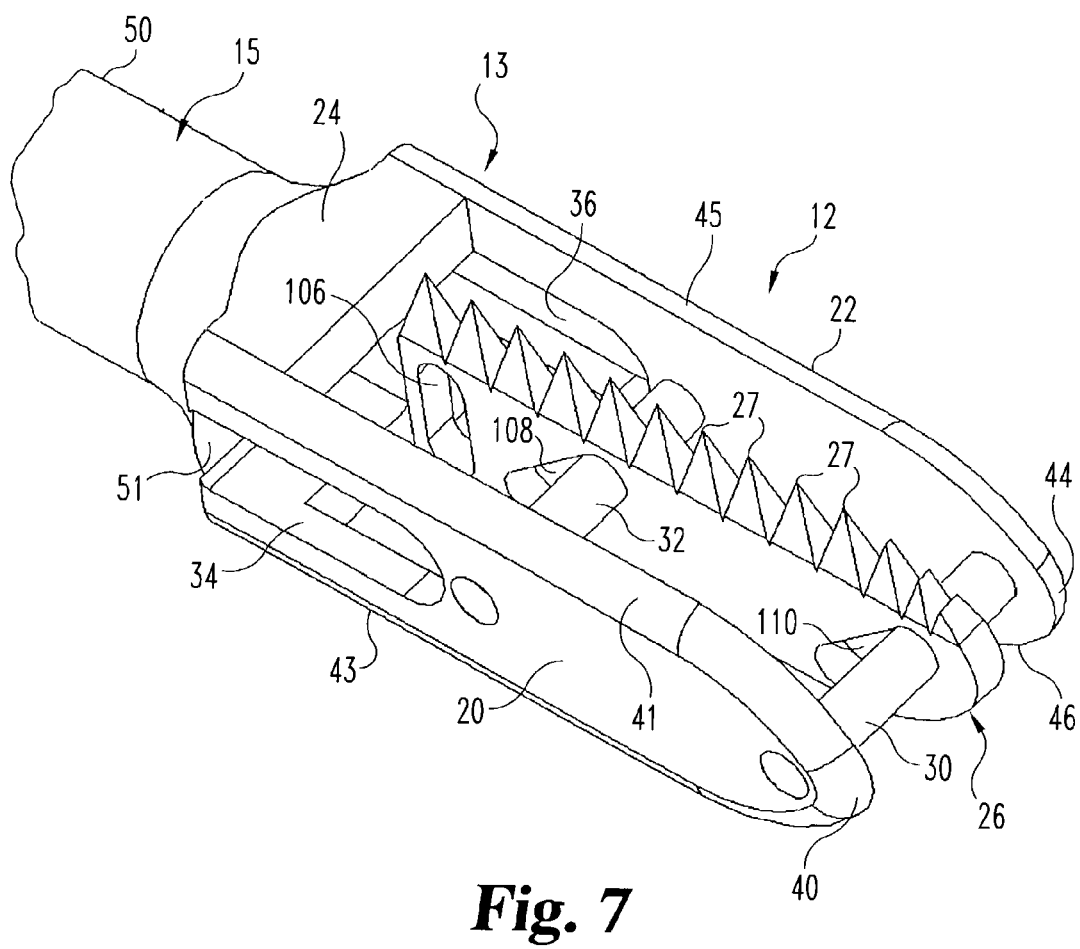
FIG. 7 is a perspective view showing the treatment member of FIG. 5 mounted to a distal portion of a mounting member of the instrument of FIG. 1.
Figure 11:
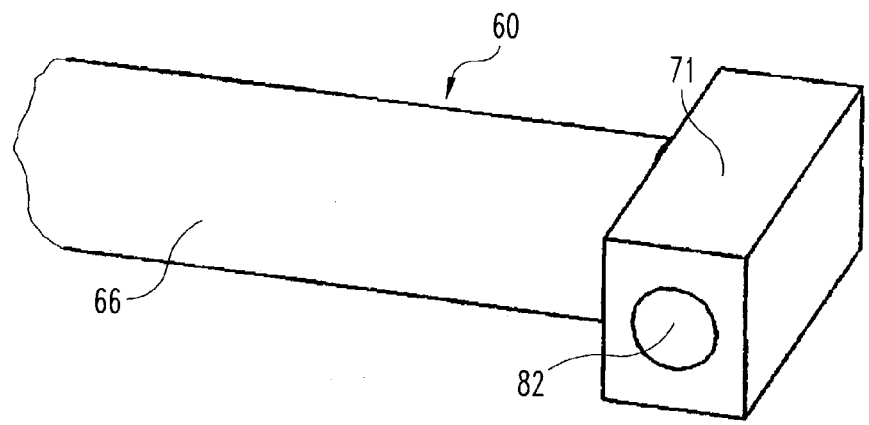
FIG. 11 is a perspective view of a portion of the distal portion of an actuating member of the treatment instrument of FIG. 1.
Figure 12:
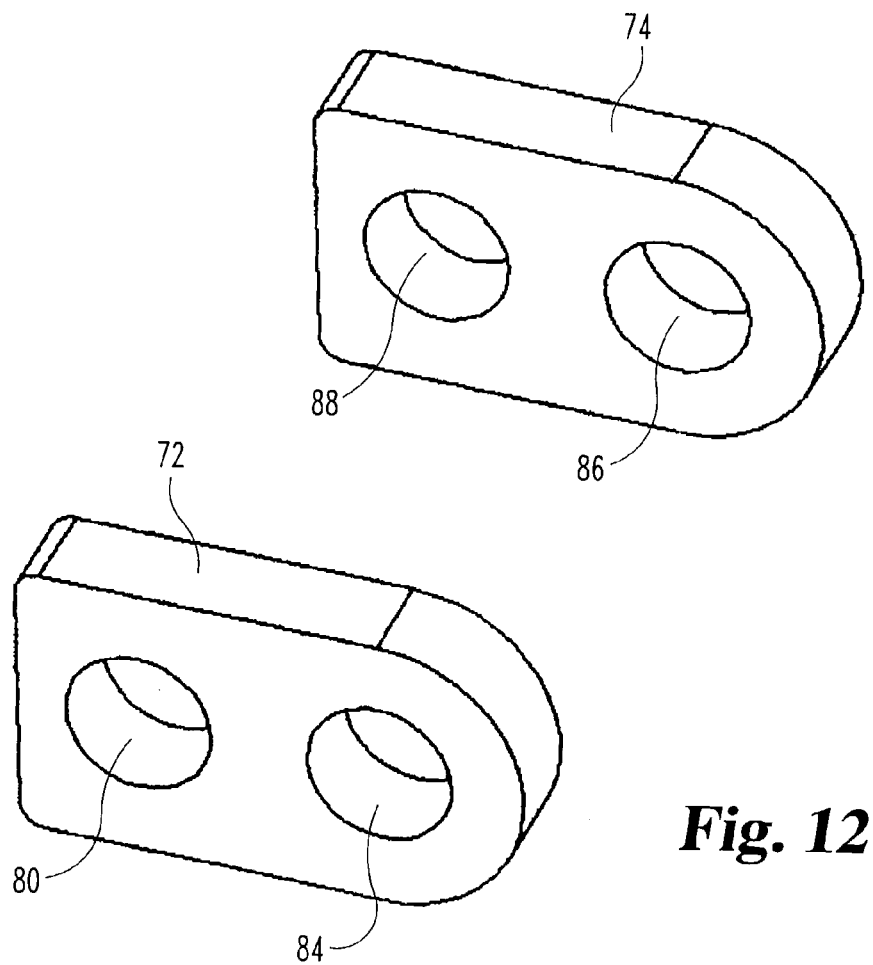
FIG. 12 is a perspective view of a pair of linkage plates engageable to the portion of the actuating member shown in FIG. 11.

As shown in FIGS. 6 and 11, an actuating member 60 is movably received in mounting member 15. Actuating member 60 includes a shaft 66 and a coupling assembly 70 at a distal end of shaft 66. Shaft 66 is positionable in a passage 57 (FIG. 9) extending through shaft 50 of mounting member 15 that opens at distal end wall 51 of end member 24. Coupling assembly 70 includes a drive member 71 extending transversely from shaft 66. A first linkage plate 72 extends from distally from one side of drive member 71, and a second linkage plate 74 extends distally from the opposite side of drive member 71. A pin 78 can be positioned through proximal hole 80 (FIG. 12) of first linkage plate 72 to couple linkage plate 72 to drive member 71. A similar pin can pass through proximal hole 88 (FIG. 12) of linkage plate 74 to couple linkage plate 74 to the other side of drive member 71. A linkage member 76 extends between linkage plates 72, 74, and is spaced distally from drive member 71. Linkage member 76 can be secured in distal holes 84, 86 of linkage plates 72, 74.

When assembled, treatment members 26, 28 are coupled to coupling assembly 70 and positioned between and movable relative to flange members 20, 22 by movement of actuating member 60. Treatment members 26, 28 are movably mounted to flange members 20, 22 with distal guide pin 30 extending through distal passages 110, and proximal guide pin 32 extending through proximal passages 108. Linkage member 76 of coupling assembly 70 extends through proximal slots 106, and linkage plates 72, 74 are received in respective ones of the side openings 34, 36. Drive member 71 of coupling assembly 70 is positioned distally of distal end wall 51 of end member 24 between flange members 20, 22. Drive member 71 is larger than the opening of passage 57 at the distal end of shaft 50, and can contact distal end wall 51 to limit proximal movement of coupling assembly 70 and thus actuating member 60 relative to mounting member 15.

When treatment members 26, 28 are in their undeployed position, proximal member 71 is adjacent end wall 51, guide pin 32 is located adjacent distal ends 112 of distal passages 110 and distal ends 109 of proximal passages 108. Linkage member 76 is located adjacent the upper end of proximal slots 106. In the undeployed position, treatment members 26, 28 are retracted so that treatment portions 27 are recessed at or below the upper ends 41, 45 of flange members 20, 22, and treatment portions 29 are recessed at or below the lower ends 43, 46 of flange members 20, 22, as shown in FIG. 2. In the undeployed position, the reduced height distal ends 104 of treatment members 26, 28 are substantially aligned with the rounded distal end noses of 40, 44 of flange members 20, 22, as shown in FIG. 2. This provides treatment system 12 with a tapered leading end having smooth surface profile, facilitating insertion into a spinal disc space. It is contemplated that flange members 20, 22 can facilitate recapitulation of a collapsed disc space as it is inserted therein.

When deployed, actuating member 60 is moved distally relative to mounting member 15, thereby advancing coupling assembly 70 distally between flange members 20, 22. This distal movement advances treatment members 26, 28 along guide pins 30, 32 until guide pin 32 is located adjacent proximal ends 113 of distal passages 110 and proximal ends 111 of proximal passages 108. The inclination of passages 108, 110 relative to longitudinal axis 101 of treatment members 26, 28 causes treatment members 26, 28 to move upwardly and downwardly, respectively, advancing treatment portions 27, 29 beyond the upper ends 41, 45 and lower ends 43, 46 of flange members 20, 22. Linkage plates 72, 74 are simultaneously advanced distally in side openings 34, 36.

As shown in FIGS. 3 and 4, treatment members 26 are moved upwardly through the upper opening between flange members 20, 22 when moving to the deployed position, and treatment members 28 are moved downwardly through the lower opening between flange members 20, 22 when moving to the deployed position. Treatment members 26, 28 also move distally relative to flange members 20, 22 so that distal ends 104 extend distally past distal ends 40, 44 of flange members 20, 22 through the distal opening between flange members 20, 22. It is contemplated that treatment members 26, 28 move parallel to longitudinal axis 11 of treatment instrument 10 so that the entire length of treatment members 26, 28 contacts the adjacent vertebral endplate to provide treatment thereto when deployed.

The mounting arrangement between mounting portion 13 and treatment members 26, 28 facilitates the application of sufficient force to treatment members 26, 28 so that treatment portions 27, 29 can penetrate and/or crush the adjacent bony structure when deployed. Guide pins 30, 32 provide multiple support locations in the passages 110, 108 of treatment members 26, 28 to maintain parallel movement of the treatment members 26, 28 relative to longitudinal axis 11 throughout the range of motion between deployed and undeployed positions.

Distal movement of actuating member 60 in mounting member 15 can be limited by any one or combination of contact of the guide pins 30, 32 with the proximal ends of passages 110, 108; contact of linkage member 76 with the end of slot 106 opposite the respective treatment portions 27, 29; contact of linkage plates 72, 74 with the distal ends of side opening 34, 36; with an arrangement between the proximal ends of mounting member 15 and actuating member 60; or with the handle assembly 16.

Figure 13:
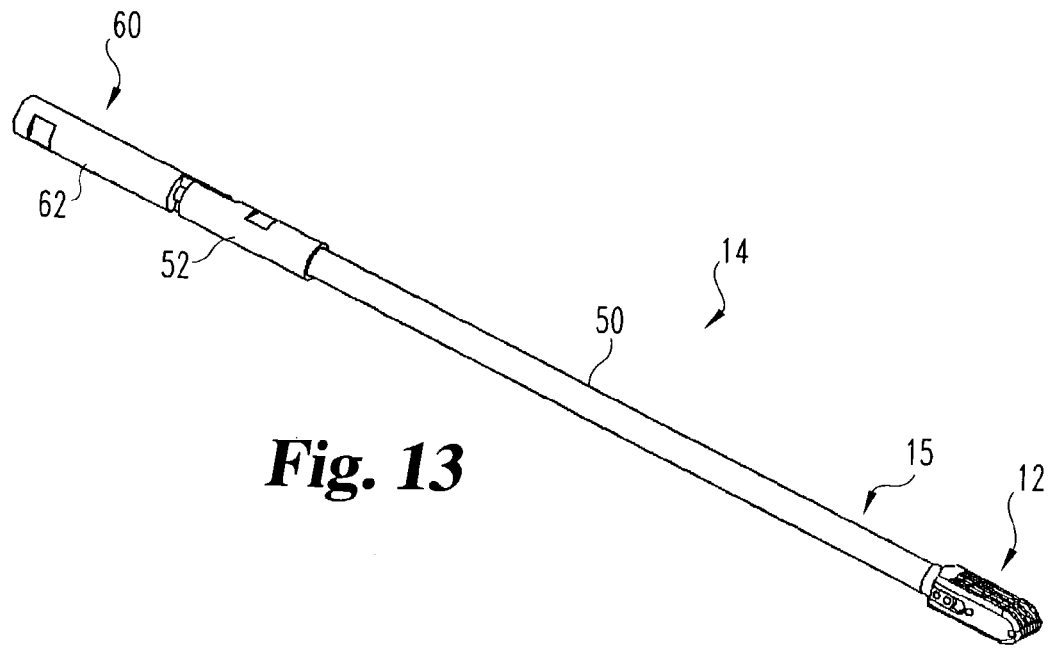
FIG. 13 is a perspective view showing the assembly of the actuating member, mounting member and treatment members of the treatment instrument of FIG. 1 with the handle assembly removed.
Figure 14:
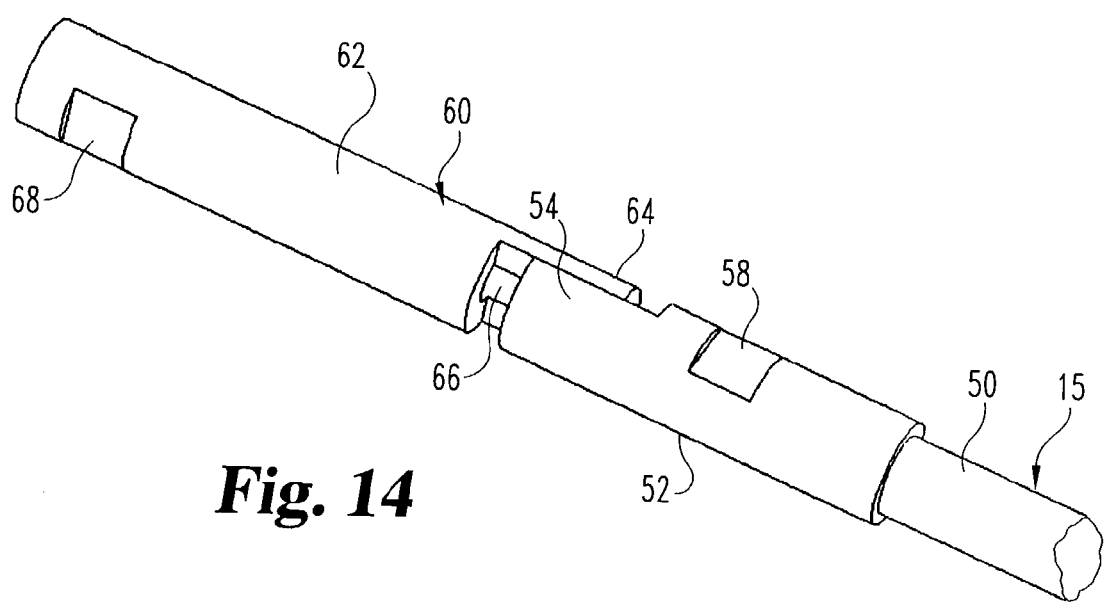
FIG. 14 is a perspective view of a boss assembly at a proximal end of the portion of the treatment instrument shown in FIG. 13.

Referring now to FIGS. 13-14, the proximal ends of actuating assembly 14 will be discussed. Actuating assembly 14 includes mounting member 15 and actuating member 60 movably received in passage 57 (FIG. 9) extending through shaft 50 of mounting member 15. Mounting member 15 includes a boss 52 at a proximal end of shaft 50, and actuating member 60 includes a boss 62 at a proximal end of shaft 66. Boss 52 includes a proximal extension 54 extending partially around passage 57, and boss 62 includes a distal extension 64 extending partially around shaft 66. Distal extension 64 is movable along proximal extension 54. Proximal movement of shaft 66 relative to shaft 50 can be limited by, for example, contact of proximal member 71 with distal end wall 51, to maintain extensions 54, 64 in an overlapping arrangement. Distal movement of shaft 66 relative to shaft 50 can be limited by, for example, contact of boss 62 with boss 52.

Extensions 54, 64 contact one another to resist inner shaft 66 from rotating within passage 57. Proximal boss 62 can include a first notch 68 formed in a first side thereof and a second opposing notch (not shown) in the opposite side. Proximal boss 52 can include a first notch 58 formed in a first side thereof and a second opposing notch (not shown) in the opposite side. As discussed further below, notches 58, 68 facilitate attachment of handle assembly 16 to bosses 52, 62.

Figure 15:
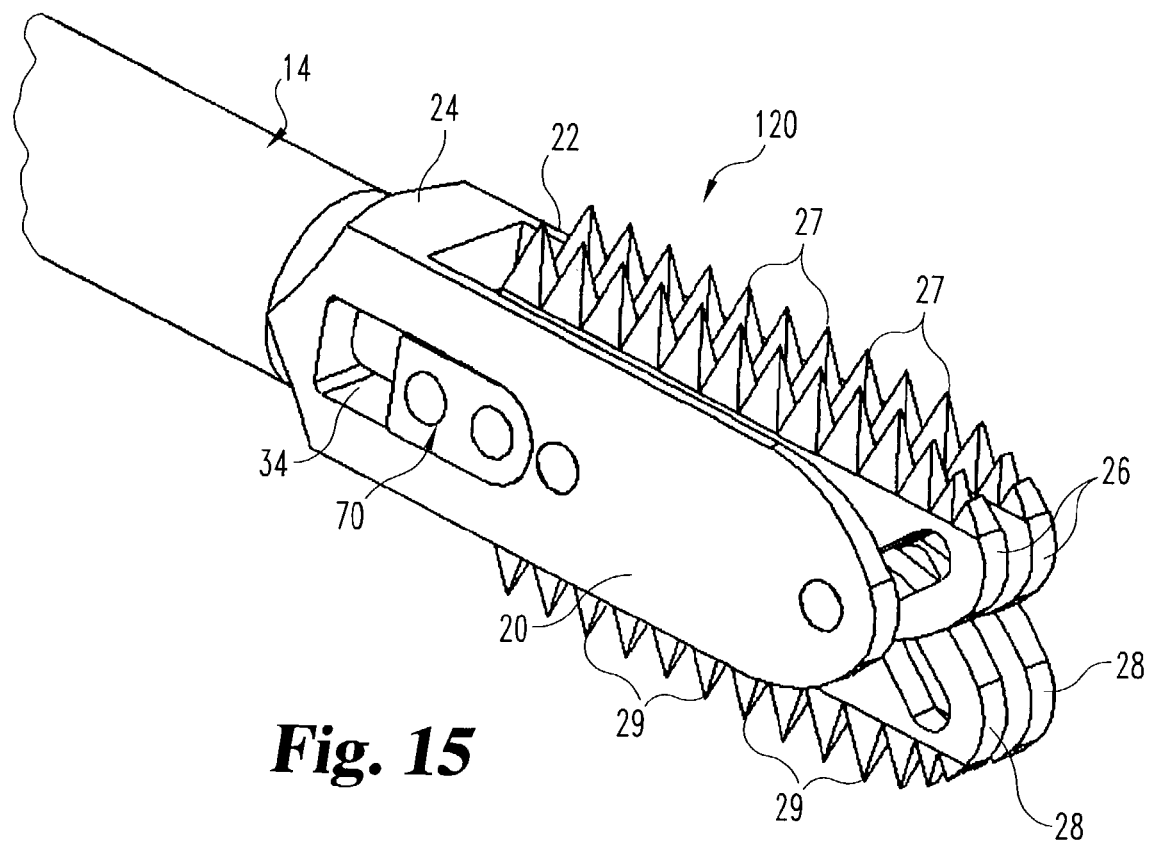
FIG. 15 is a perspective view of another embodiment distal end portion for the treatment instrument of FIG. 1 with the treatment members in a deployed position.

Referring to FIG. 15, another embodiment treatment system 120 includes treatment members 26 with treatment portions 27 projecting upwardly from flange members 20, 22 and treatment members 28 with treatment portions 29 projecting downwardly from flange members 20, 22. In the illustrated embodiment, four treatment members 26, 28 are provided and alternate with one another so that every other one of the treatment members extends upwardly or downwardly. By providing fewer treatment members 26, 28, the width between flange members 20, 22 can be reduced facilitating the use of treatment instrument 10 in minimally invasive surgical techniques. Other embodiments contemplate other numbers of treatment members, including one treatment member up to ten or more treatment members. In embodiments with multiple treatment members, the treatment portions of adjacent treatment members can extend in opposite directions as shown. It is further contemplated that two or more adjacent treatment members can include treatment portions extending in the same direction.

It is contemplated that the vertebral endplate treatment instruments discussed herein can be used in minimally invasive surgical techniques where the disc space is accessed through a micro-incision, a sleeve, or one or more retractors that provide a protected passageway to the disc space. The treatment instruments also have application in open surgical techniques where skin and tissue are incised and retracted to expose the surgical site. The treatment instruments can be useful in posterior approaches to a spinal disc space where tissue, nerves, and the posterior vertebral elements hinder access to the disc space. Applications in other approaches, including anterior, anterior-oblique, lateral, and postero-lateral approaches are also contemplate. The treatment instruments also have application in procedures that access any region of the spine, including the cervical, thoracic, lumbar and sacral regions.

Figure 16:
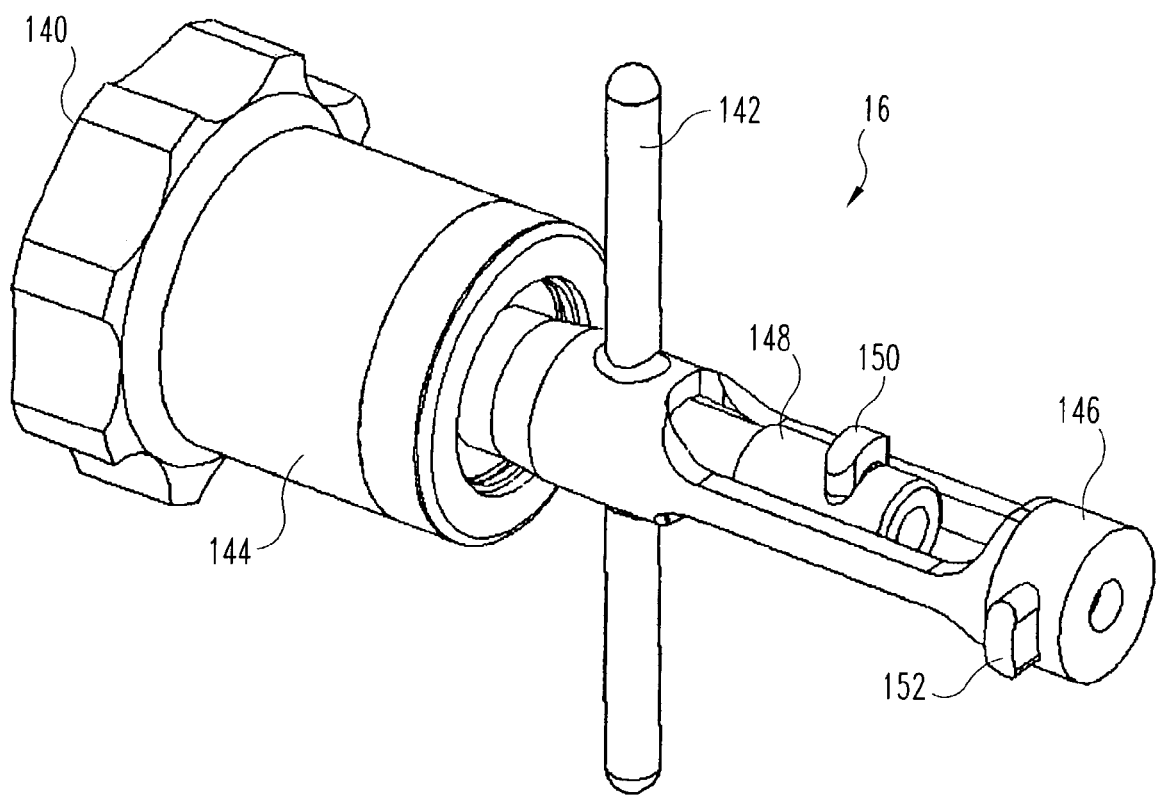
FIG. 16 is a perspective view of the handle assembly of the treatment instrument of FIG. 1.

In FIG. 16, handle assembly 16 is shown removed from the distal portion of treatment instrument 10 shown in FIG. 13. Handle assembly 16 includes a proximal knob 140 and a body 144 extending from knob 140. Handle assembly 16 further includes a fixed shaft 146 coupled to body 144, and a movable shaft 148 coupled to knob 140. Actuating member 60 is coupled to movable shaft 148 with locking member 150, and mounting member 15 is coupled to fixed shaft 146 with locking member 152. Locking members 150, 152 releasably engage notches 68, 58, respectively, to secure the distal portion of instrument 10 to handle assembly 16.

Figure 17:
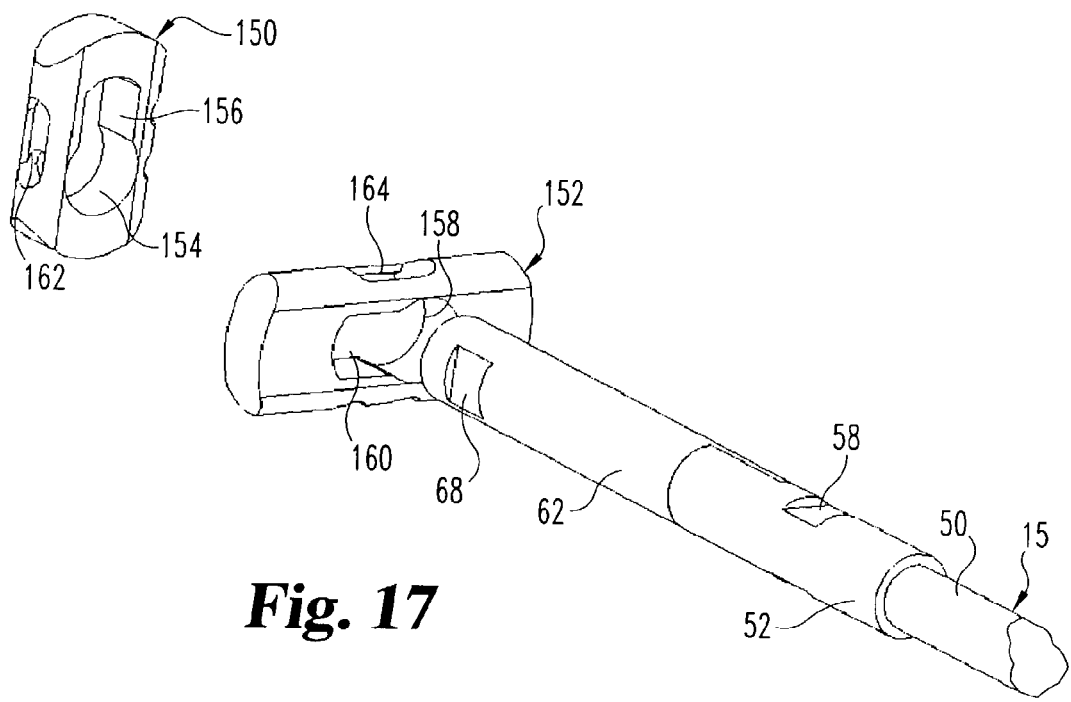
FIG. 17 is a perspective view showing the locking members of the handle assembly prior to insertion of the proximal boss members of the actuator assembly.
Figure 18:
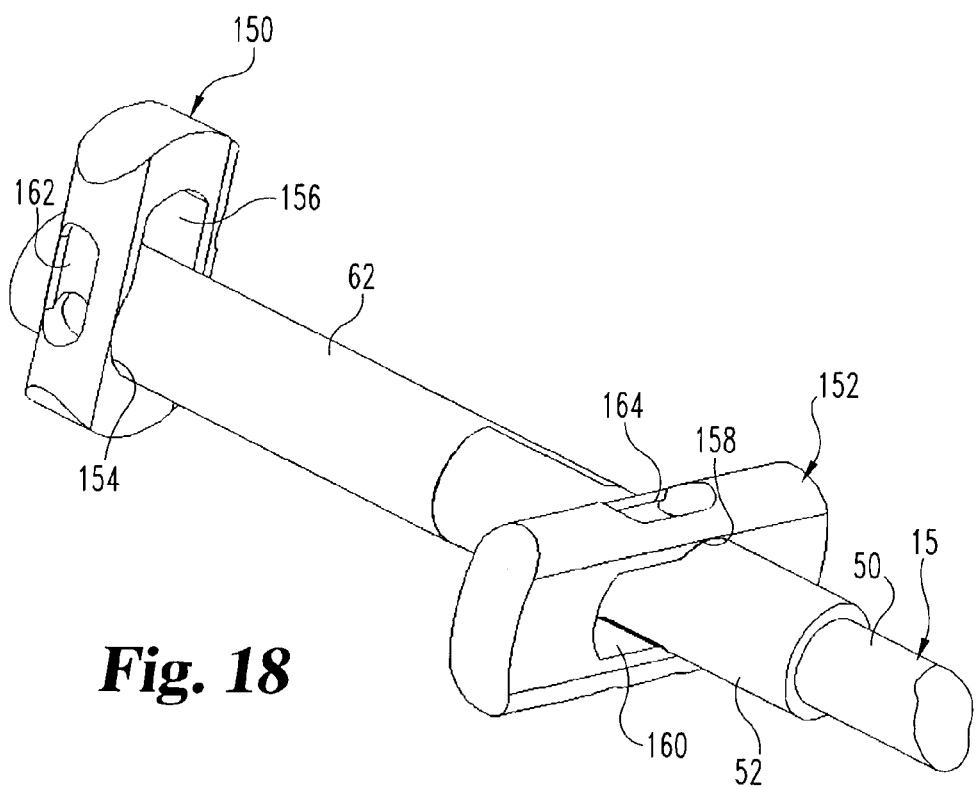
FIG. 18 is a perspective view showing the locking members of the handle assembly after insertion of the proximal boss members of the actuator assembly.
Figure 19:
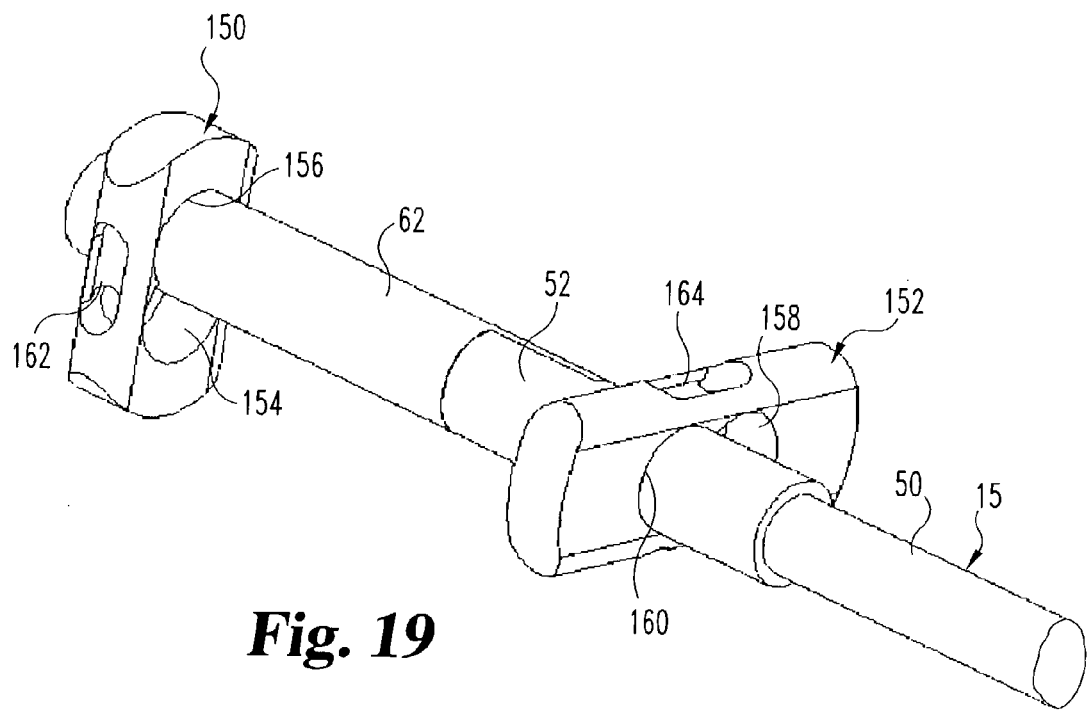
FIG. 19 is a perspective view showing the locking members of the handle assembly engaged with the proximal boss members of the actuator assembly.
Figure 20:
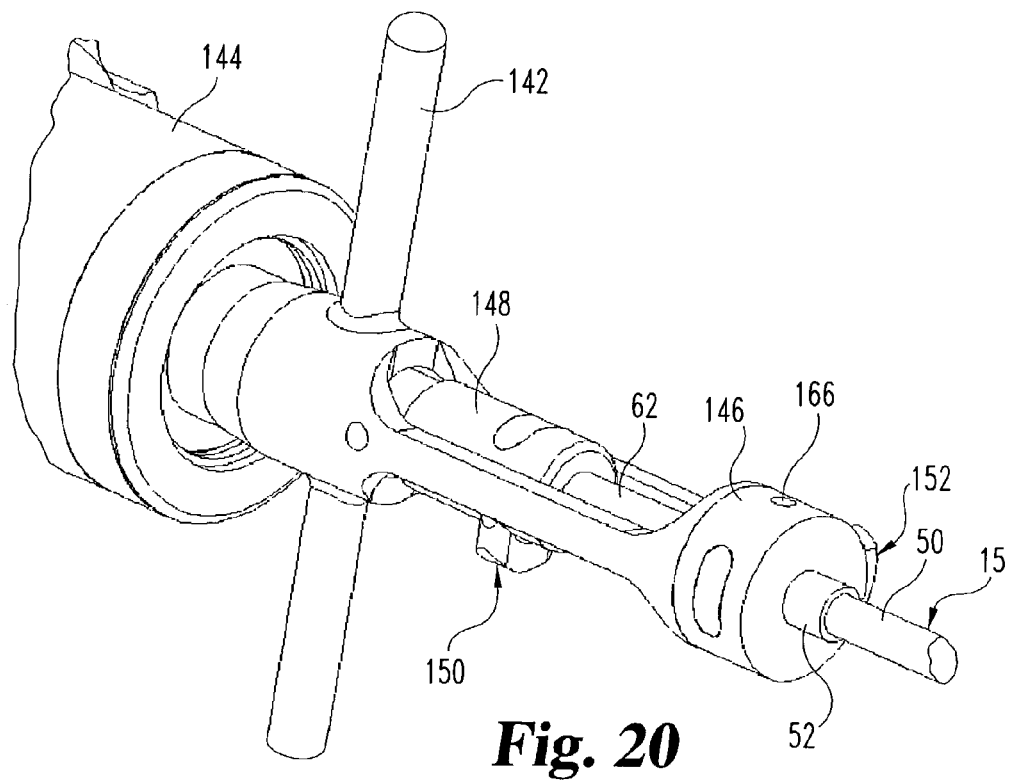
FIG. 20 is a perspective view showing the handle assembly with the locking members engaged with the proximal boss members of the actuator assembly.

Referring further to FIGS. 17-18, there is shown locking members 150, 152 without the remaining portions of handle assembly 16. In FIG. 17, locking members 150, 152 are in their unlocked position so that cylindrical passage portions 154, 158 are aligned with bosses 62, 52. Bosses 62, 52 are positionable through passage portions 154, 158 to align notches 68 with non-cylindrical passage portion 156 of locking member 150 and to align notches 58 with non-cylindrical passage portion 160 of locking member 152, as shown in FIG. 18. Locking member 150 can then be moved so that passage portion 156 engages notches 68, and passage portion 160 engages notches 58, as shown in FIGS. 19 and 20. In this engaged position, boss 62 is engaged with movable shaft 148, and boss 52 is engaged with fixed shaft 146.

Locking member 150 includes a slotted receptacle 162 that receives a pin (not shown) coupled to movable shaft 148 to movably secure locking member 150 thereto. Similarly, locking member 152 includes a slotted receptacle 164 to receive a pin 166 coupled to fixed shaft 146 to movably secure locking member 150 thereto. In the locked position of locking members 150, 152 shown in FIG. 20, one end of each of the locking members 150, 152 aligns with an outer surface of the corresponding shaft 146, 148 while the other end protrudes outwardly therefrom. The other ends of locking members 150, 152 can be depressed to align passage portions 154, 158 with bosses 62, 52 to uncouple handle assembly 16 and allow its removal therefrom.

Figure 21:
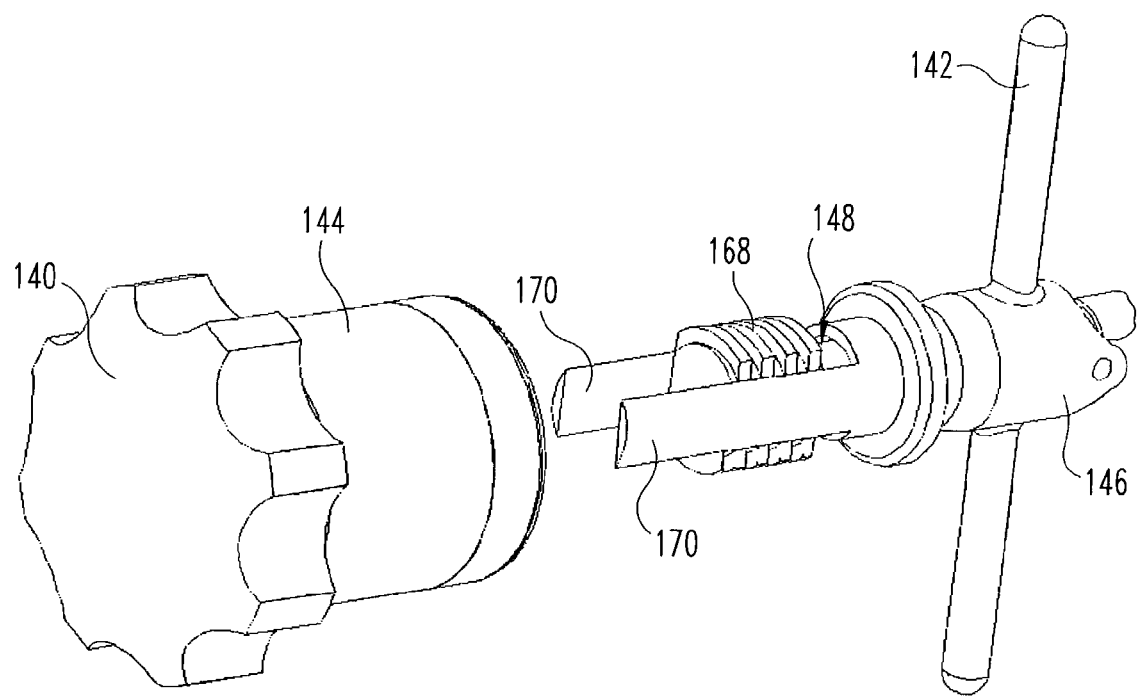
FIG. 21 is an exploded perspective view showing handle assembly of FIG. 16.

Referring to FIG. 21, knob 140 is rotatable relative to body 144 in a first direction such as, for example, counterclockwise, to axially and distally advance movable shaft 148 within fixed shaft 146. For example, movable shaft 148 can be provided with a threaded proximal end 168 that is threadingly engaged with knob 140 in body 144. The non-rotating, distal movement of movable shaft 148 distally advances actuating member 60 in mounting member 15, thus deploying treatment members 26, 28 from mounting portion 13. Rotation of knob 140 in the opposite direction moves movable shaft 148 and actuating member 60 proximally in the opposite direction to undeploy treatment members 26, 28 while maintaining mounting member 15 stationary. Fixed shaft 146 is engaged with body 144 with proximal extensions 170 that extend along threaded proximal end 168.

A torque handle 142 can be provided that extends laterally from fixed shaft 146. Torque handle 142 can be grasped by the surgeon to facilitate insertion and withdrawal of the distal end of instrument 10 from the operative site. Torque handle 142 can also assist in moving instrument 10 proximally, distally, and/or rotationally about axis 11 with treatment members 26, 28 in the deployed condition to provide further treatment of the endplates.

Figure 22:
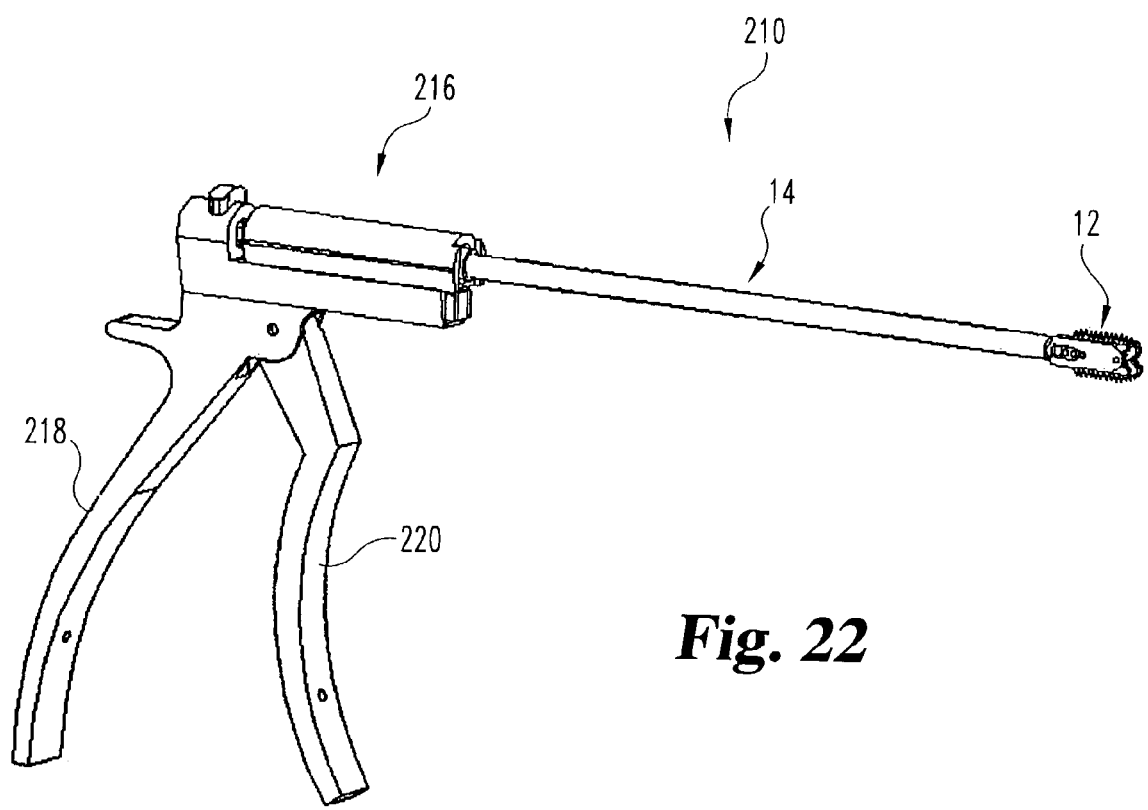
FIG. 22 is a perspective view of another embodiment endplate treatment instrument.
Figure 23:
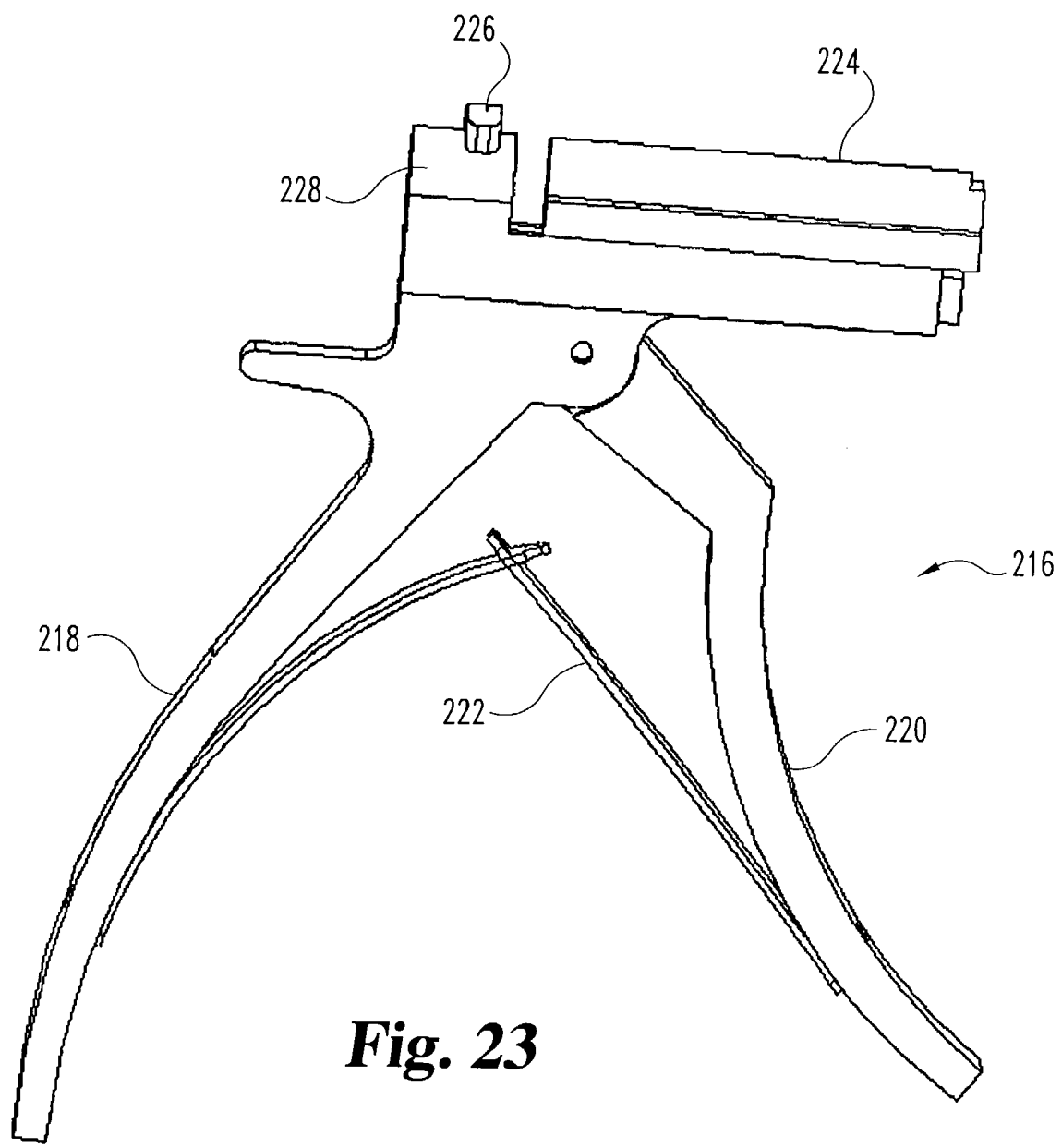
FIG. 23 is a perspective view of a proximal handle assembly provided with the treatment instrument of FIG. 22.

FIGS. 22-23 show another embodiment treatment instrument 210 which can be identical to treatment instrument 10 above except for handle assembly 216. Handle assembly 216 employs a handle and lever arrangement to move actuating member 60 relative to mounting member 15. Handle assembly 216 includes a fixed handle 218 and a movable handle 220. Movable handle 220 can be coupled to a linkage 228 proximal of housing 224. Linkage 228 is coupled to the proximal end of actuating member 60 by, for example, a locking member 226 releasably engaged with notch 68 in proximal boss 62 in the manner discussed above with respect to handle assembly 16. Fixed handle 218 is fixedly coupled to housing 224, which is fixedly coupled to the proximal end of mounting member 15. A leaf spring 222 can be provided between handles 218, 220 to bias movable handle 220 away from fixed handle 218, and thus normally positioning treatment members 26, 28 to the undeployed position for insertion and withdrawal from the operative site. Handle 220 is moved toward handle 218 to distally advance actuating member 60 relative to mounting member 15 and thereby deploy treatment member 26, 28 from mounting portion 13.

While the invention has been illustrated and described in detail in the drawings and foregoing description, the same is to be considered as illustrative and not restrictive in character. All changes and modifications that come within the spirit of the invention are desired to be protected.

What is claimed is:

1. A vertebral endplate treatment instrument, comprising:
a handle assembly;
an actuating assembly extending distally from said handle assembly along a longitudinal axis, said actuating assembly including a distal mounting portion;
a treatment system at a distal end of said actuating assembly, said treatment system including at least one treatment member mounted in said mounting portion and movable in parallel relation away from said longitudinal axis from an undeployed position to a deployed position by displacing said actuating assembly along said longitudinal axis, wherein said at least one treatment member includes a plurality of treatment portions adapted to at least partially penetrate a vertebral endplate in said deployed position and in said undeployed position said at least one treatment member is substantially enclosed in said mounting portion to reduce contact by said plurality of treatment portions with tissue and wherein said at least one treatment member moves parallel to the longitudinal axis between the undeployed and deployed positions, wherein said actuating assembly includes:
  a mounting member including said distal mounting portion to which said at least one treatment member is movably mounted;
  an actuating member movable relative to said mounting member from a first position wherein said at least one treatment member is in said undeployed position to a second position wherein said at least one treatment member is in said deployed position, said actuating member including a shaft and a coupling assembly at a distal end of said shaft in said mounting portion, said coupling assembly including a linkage member;
  said mounting member includes a shaft defining a passage for receiving said actuating member, said mounting portion including:
  a first flange member and a second flange member spaced from said first flange member, said at least one treatment member being positioned between said first and second flange members;
  a distal guide member extending between said first and second flange members; and
  a proximal guide member extending between said first and second flange members, wherein said distal guide member, said proximal guide member, and said linkage member are coupled to said at least one treatment member and act thereon to move said at least one treatment member between said deployed and undeployed positions.

2. The instrument of claim 1, wherein said plurality of treatment portions are in the form of spikes having an outwardly extending pointed end.

3. The instrument of claim 1, wherein said at least one treatment member includes:
  a body portion extending along a longitudinal axis between a proximal end and a distal end; and
  said plurality of treatment portions extend along one side of said body portion between said proximal end and said distal end.

4. The instrument of claim 3, wherein said distal end of said body portion includes a tapered nose.

5. The instrument of claim 3, wherein said body portion includes a distal passage oriented transversely to said longitudinal axis of said body portion and a proximal passage oriented transversely to said longitudinal axis of said body portion.

6. The instrument of claim 5, wherein:
  said distal passage includes a distal end offset from said longitudinal axis toward said plurality of treatment portions and a proximal end offset from said longitudinal axis toward a side of said body opposite said treatment portions; and
  said proximal passage includes a distal end offset from said longitudinal axis toward said plurality of treatment portions and a proximal end offset from said longitudinal axis toward a side of said body opposite said treatment portions.

7. The instrument of claim 6, wherein said body portion includes a slot orthogonally oriented to said longitudinal axis of said body portion and located proximally of said proximal passage.

8. The instrument of claim 7, wherein:
  said distal guide member extends through said distal passage of said body portion, said proximal guide member extends through said proximal passage of said body portion, and said linkage member extends through said proximal slot of said body portion.

9. The instrument of claim 8, wherein said coupling assembly includes a drive member and a pair of linkage plates extending distally from opposite sides of said drive member, said linkage member extending between said linkage plates distally of said drive member.

10. The instrument of claim 1, wherein said at least one treatment member comprises a second treatment member movable simultaneously therewith from a deployed position to an undeployed position with said actuating system, said second treatment member including a plurality of treatment portions extending in a direction opposite said plurality of treatment portions of said at least one member, said plurality of treatment portions being adapted to at least partially penetrate an adjacent vertebral endplate in said deployed position.

11. The instrument of claim 10, wherein each of said treatment members includes:
  a body portion extending along a longitudinal axis between a proximal end and a distal end; and
  said plurality of treatment portions extend along one side of said body portion between said proximal end and said distal end.

12. The instrument of claim 11, wherein for each of said treatment members:
  said body portion includes a distal passage oriented transversely to said longitudinal axis of said body portion and a proximal passage oriented transversely to said longitudinal axis of said body portion.

13. The instrument of claim 12, wherein for each of said treatment members:
  said distal passage includes a distal end offset from said longitudinal axis toward said plurality of treatment portions and a proximal end offset from said longitudinal axis toward a side of said body opposite said treatment portions; and
  said proximal passage includes a distal end offset from said longitudinal axis toward said plurality of treatment portions and a proximal end offset from said longitudinal axis toward a side of said body opposite said treatment portions.

14. The instrument of claim 13, wherein for each of said treatment members:
  said body portion includes a slot orthogonally oriented to said longitudinal axis of said body portion and located proximally of said proximal passage.

15. The instrument of claim 14, wherein:
  said distal guide member extends through said distal passage of said body portion of each of said treatment members, said proximal guide member extends through said proximal passage of said body portion of each of said treatment members, and said linkage member extends through said proximal slot of said body portion of each of said treatment members.

16. The instrument of claim 10, wherein for each of said treatment members:
  a distal end of said treatment members includes a tapered nose, wherein in said undeployed position said noses are substantially aligned with one another along a longitudinal axis of the treatment instrument and in said deployed position each of said noses are advanced distally and offset from one another on opposite sides of the longitudinal axis of the treatment instrument.

17. The instrument of claim 10, wherein each of said treatment members moves parallel to the longitudinal axis between the undeployed and deployed positions.

18. The instrument of claim 1, wherein said at least one treatment member includes a plurality of treatment members positioned in side-by-side relation, each of which include a plurality of treatment portions, wherein said treatment portions of adjacent ones of said treatment members extend in opposite directions.

19. The instrument of claim 1, wherein said first and second flange members define an upper opening and a lower opening therebetween, wherein in said deployed position said plurality of treatment portions extend through one of said upper and lower openings.

20. The instrument of claim 19, wherein said first and second flange members further define a distal opening and in said deployed position said at least one treatment member extends through said distal opening.

21. The instrument of claim 19, wherein in said undeployed position said at least one treatment member is positioned entirely between said first and second flange members.

22. A vertebral endplate treatment instrument, comprising:
a handle assembly;
an actuating assembly extending distally from said handle assembly along a longitudinal axis; and
a treatment system at a distal end of said actuating assembly, said treatment system including at least one treatment member extending along a longitudinal axis from a proximal end to a distal end, wherein said at least one treatment member is movable away from said longitudinal axis with said actuating assembly from an undeployed position to a deployed position with said longitudinal axis of said at least one treatment member remaining generally parallel with said longitudinal axis of said actuating assembly and said at least one treatment member is adapted to move distally along said longitudinal axis toward said deployed position with said distal end of said at least one treatment member extending distally beyond said distal end of said actuating assembly, wherein said at least one treatment member includes:
a body portion extending along said longitudinal axis of said at least one treatment member between a proximal end and a distal end, said body portion including a plurality of treatment portions extending along one side of said body portion between said proximal end and said distal end, wherein said body portion includes a distal passage oriented transversely to said longitudinal axis of said body portion and a proximal passage oriented transversely to said longitudinal axis of said body portion, said distal passage includes a distal end offset from said longitudinal axis toward said plurality of treatment portions and a proximal end offset from said longitudinal axis toward a side of said body opposite said treatment portions and said proximal passage includes a distal end offset from said longitudinal axis toward said plurality of treatment portions and a proximal end offset from said longitudinal axis toward a side of said body opposite said treatment portions, wherein said body portion includes a slot orthogonally oriented to said longitudinal axis of said body portion and located proximally of said proximal passage;
wherein said actuating assembly includes:
a mounting member including a distal mounting portion to which said at least one treatment member is movably mounted; and
an actuating member movable relative to said mounting member from a first position wherein said at least one treatment member is in said undeployed position and substantially enclosed in said mounting portion to reduce contact by said plurality of treatment portions with tissue to a second position wherein said at least one treatment member is in said deployed position.

23. The instrument of claim 22, wherein said plurality of treatment portions are adapted to at least partially penetrate a vertebral endplate in said deployed position.

24. The instrument of claim 22, wherein said at least one treatment member comprises a second treatment member extending along a longitudinal axis and movable simultaneously with said at least one treatment member from a deployed position to an undeployed position with said actuating system.

25. The instrument of claim 24, wherein said longitudinal axis of each of said treatment members moves parallel to said longitudinal axis of said actuator assembly between said undeployed and deployed positions.

26. The instrument of claim 25, wherein said treatment members each include a plurality of treatment portions, said plurality of treatment portions of said at least one treatment member being oriented in a direction opposite the plurality of treatment portions of said second treatment member, said plurality of treatment portions being adapted to at least partially penetrate an adjacent vertebral endplate in said deployed position.

27. The instrument of claim 22, wherein:
said actuating member includes a shaft and a coupling assembly at a distal end of said shaft in said mounting portion, said coupling assembly including a linkage member;
said mounting member includes a shaft defining a passage for receiving said actuating member, said mounting portion including:
a first flange member and a second flange member spaced from said first flange member, said at least one treatment member being positioned between said first and second flange members;
a distal guide member extending between said first and second flange members; and
a proximal guide member extending between said first and second flange members, wherein said distal guide member extends through said distal passage of said body portion, said proximal guide member extends through said proximal passage of said body portion, and said linkage member extends through said proximal slot of said body portion.

28. The instrument of claim 27, wherein said coupling assembly includes a drive member and a pair of linkage plates extending distally from opposite sides of said drive member, said linkage member extending between said linkage plates distally of said drive member.

29. A vertebral endplate treatment instrument, comprising:
a handle assembly;
an actuating assembly extending distally from said handle assembly;
a treatment system at a distal end of said actuating assembly, said treatment system including at least one treatment member extending along a longitudinal axis, wherein said at least one treatment member includes a body portion extending along said longitudinal axis of said at least one treatment member between a proximal end and a distal end, said body portion including a first side surface and an opposite second side surface extending along said longitudinal axis and said at least one treatment member includes a plurality of treatment portions extending between said first and second side surfaces and between said proximal and distal ends of said body portion, said body portion further including a distal passage defining an elongated first opening along each of said first and second surfaces that is obliquely oriented to said longitudinal axis of said body portion and a proximal passage defining an elongated second opening along each of said first and second surfaces that is obliquely oriented to said longitudinal axis, wherein said body portion includes a slot opening at said first and second side surfaces and orthogonally oriented to said longitudinal axis of said body portion and located proximally of said proximal passage;

wherein said actuating assembly includes:
  a mounting member including a distal mounting portion to which said at least one treatment member is movably mounted; and
  an actuating member movable relative to said mounting member from a first position wherein said at least one treatment member is in an undeployed position to a second position wherein said at least one treatment member is in a deployed position, said actuating member including a shaft and a coupling assembly at a distal end of said shaft in said mounting portion, said coupling assembly including a linkage member;

said mounting member includes a shaft defining a passage for receiving said actuating member, said mounting portion including:
  a first flange member and a second flange member spaced from said first flange member, said at least one treatment member being positioned between said first and second flange members, wherein said first and second flange members substantially enclose said at least one treatment member in said undeployed position to prevent said plurality of treatment portions from contacting tissue;
  a distal guide member extending between said first and second flange members; and
  a proximal guide member extending between said first and second flange members, wherein said distal guide member extends through said distal passage of said body portion, said proximal guide member extends through said proximal passage of said body portion, and said linkage member extends through said proximal slot of said body portion.

30. The instrument of claim 29, wherein said at least one treatment member is movable with said actuating assembly from said undeployed position to said deployed position with said longitudinal axis of said at least one treatment member remaining generally parallel with a longitudinal axis of said actuating assembly.

31. The instrument of claim 29, wherein said plurality of treatment portions are adapted to at least partially penetrate a vertebral endplate in said deployed position.

32. The instrument of claim 29, wherein said at least one treatment member comprises a second treatment member movable simultaneously therewith from a deployed position to an undeployed position with said actuating system, said second treatment member including a plurality of treatment portions along a body portion thereof extending in a direction opposite of said plurality of treatment portions of said at least one treatment member.

33. The instrument of claim 32, wherein each of said treatment members moves parallel to a longitudinal axis of said actuator assembly between the undeployed and deployed positions.

34. The instrument of claim 29, wherein:
  said distal passage includes a distal end offset from said longitudinal axis toward said plurality of treatment portions and a proximal end offset from said longitudinal axis toward a side of said body opposite said treatment portions; and
  said proximal passage includes a distal end offset from said longitudinal axis toward said plurality of treatment portions and a proximal end offset from said longitudinal axis toward a side of said body opposite said treatment portions.

35. A vertebral endplate treatment instrument, comprising:
a handle assembly;
an actuating assembly extending distally from said handle assembly along a longitudinal axis; and
a treatment system at a distal end of said actuating assembly, said treatment system including at least a first treatment member and a second treatment member movable simultaneously with said first treatment member in parallel relation away from said longitudinal axis from an undeployed position to a deployed position, wherein:
  for each of said first treatment member and said second treatment member a distal end includes a tapered nose, wherein in said undeployed position said noses are substantially aligned with one another along a longitudinal axis of the treatment instrument and in said deployed position each of said noses are advanced distally and offset from one another on opposite sides of the longitudinal axis of the treatment instrument;
  said at least first and second treatment members include a plurality of treatment portions extending in a direction opposite one another and adapted to at least partially penetrate a vertebral endplate in said deployed position;
  said at least first and second treatment members move parallel to the longitudinal axis between the undeployed and deployed positions;
wherein said actuating assembly includes:
a mounting member including a distal mounting portion to which said at least first treatment member and said second treatment member are movably mounted; and
an actuating member movable relative to said mounting member from a first position wherein said at least first treatment member and said second treatment member are in said undeployed position and substantially enclosed by said mounting portion to reduce contact by said plurality of treatment portions with tissue to a second position wherein said at least first treatment member and said second treatment member are in said deployed position.

36. The instrument of claim 35, wherein said plurality of treatment portions are in the form of spikes having an outwardly extending pointed end.

37. The instrument of claim 35, wherein said first treatment member includes a body portion extending along a longitudinal axis between a proximal end and a distal end and said second treatment member includes a body portion extending along a longitudinal axis from a proximal end to a distal end.

38. The instrument of claim 37, wherein each of said body portions includes a distal passage oriented transversely to said longitudinal axes of said body portions and a proximal passage oriented transversely to said longitudinal axes of said body portions.

39. The instrument of claim 38, wherein:
  each of said distal passages includes a distal end offset from said longitudinal axes toward said plurality of treatment portions and a proximal end offset from said longitudinal axes toward a side of said bodies opposite said treatment portions; and each of said proximal passages includes a distal end offset from said longitudinal axes toward said plurality of treatment portions and a proximal end offset from said longitudinal axes toward a side of said bodies opposite said treatment portions.

40. The instrument of claim 39, wherein each of said body portions includes a slot orthogonally oriented to said longitudinal axes of said body portions and located proximally of said proximal passages.

41. The instrument of claim 40, wherein:
said actuating member includes a shaft and a coupling assembly at a distal end of said shaft in said mounting portion, said coupling assembly including a linkage member;
said mounting member includes a shaft defining a passage for receiving said actuating member, said mounting portion including:
  a first flange member and a second flange member spaced from said first flange member, said at least first treatment member and said second treatment member being positioned between said first and second flange members;
  a distal guide member extending between said first and second flange members; and
  a proximal guide member extending between said first and second flange members, wherein said distal guide member extends through said distal passages of said body portions, said proximal guide member extends through said proximal passages of said body portions, and said linkage member extends through said proximal slots of said body portions.

42. The instrument of claim 41, wherein said coupling assembly includes a drive member and a pair of linkage plates extending distally from opposite sides of said drive member, said linkage member extending between said linkage plates distally of said drive member.

* * * * *